United States Patent [19]

Nelson

[11] Patent Number: 4,534,756

[45] Date of Patent: Aug. 13, 1985

[54] FAULT DETECTION APPARATUS AND METHOD FOR PARENTERAL INFUSION SYSTEM

[75] Inventor: Peter E. Nelson, Mountain View, Calif.

[73] Assignee: Ivac Corporation, San Diego, Calif.

[21] Appl. No.: 483,903

[22] Filed: Apr. 11, 1983

[51] Int. Cl.³ ............................................. H61M 5/00
[52] U.S. Cl. ........................................ 604/50; 604/65
[58] Field of Search ....................... 604/50, 65, 66, 67, 604/245

[56] References Cited

U.S. PATENT DOCUMENTS

| | | | |
|---|---|---|---|
| 3,871,361 | 3/1975 | Kamen | 604/66 X |
| 4,080,966 | 3/1978 | McNally et al. | 604/50 |
| 4,098,274 | 7/1978 | Ebling et al. | 604/65 X |
| 4,213,454 | 7/1980 | Shim | 604/65 |
| 4,309,993 | 1/1982 | Brown | 604/50 X |
| 4,394,862 | 7/1983 | Shim | 604/67 |
| 4,431,425 | 2/1984 | Thompson et al. | 604/245 X |

Primary Examiner—Edward M. Coven
Attorney, Agent, or Firm—Fulwider, Patton, Rieber, Lee & Utecht

[57] ABSTRACT

Apparatus and related method for use in a parenteral administration system, for detecting fault conditions such as an infiltration, an open fluid line or an air bubble in the fluid line. The apparatus is particularly adapted for use with a parenteral administration system of the type that includes a pulsing infusion device for incrementally infusing fluid through a fluid tube to a patient's venous or arterial system. The apparatus qualitatively evaluates the pressure in the fluid tube to detect characteristic patterns indicative of each such fault condition and actuates an alarm whenever one is detected.

53 Claims, 8 Drawing Figures

Fig. 1

Fig. 7
OPEN LINE DETECTOR-37

Fig. 8
TIMING DIAGRAM — OPEN LINE DETECTOR (a) MOTOR STEP SIGNAL
(b) PRESSURE SIGNAL (NORMAL)
(c) PRESSURE SIGNAL (OPEN LINE)

FAULT DETECTION APPARATUS AND METHOD FOR PARENTERAL INFUSION SYSTEM

BACKGROUND OF THE INVENTION

This invention relates generally to systems for administering parenteral fluids to a patient, and, more particularly, to systems of this type having an infusion apparatus for infusing the fluid into the patient's vascular system.

Systems of this particular type have enjoyed widespread usage in hospitals for administering parenteral fluids at precise rates. The systems are useful for both venous and arterial infusions and typically include an infusion pump and an associated controlling device for pumping the parenteral fluid through a fluid tube and needle to the patient's vein or artery.

One drawback to conventional infusion pump systems of this type is that the needle can sometimes become dislodged from the patient's vein or artery. This will normally cause an increase in back pressure, but the pump will nevertheless continue to pump fluid at substantially the same fixed rate. The fluid therefore can infiltrate into the patient's body tissue and cause severe damage. Similarly, the needle can sometimes become dislodged from the patient entirely, yet the pump will continue to pump the fluid at the same fixed rate.

One known prior technique for detecting fluid infiltrations is to monitor the patient's skin temperature in the vicinity of the needle. Since the parenteral fluid is ordinarily cooler than the patient's body temperature, and since the fluid is not carried away as rapidly when an infiltration occurs, an infiltration will ordinarily create a temperature drop in the vicinity of the needle. Thus, whenever a drop in skin temperature is detected, it is deduced that an infiltration is occurring. This technique is not believed to have proven completely satisfactorily in all circumstances, such as, for example, when the parenteral fluid has a temperature substantially the same as that of the patient's blood.

Other known prior techniques for detecting an infiltration of a parenteral fluid into a patient's body tissue involve intervention by hospital personnel. In one such technique, an attendant visually inspects the region around the needle, to detect any swelling that might indicate an infiltration. In another technique, useful only when the fluid is being administered from a bottle under the force of gravity, the attendant periodically lowers the bottle to an elevation below the needle such that fluid flows outwardly from the patient. If when this is done the patient's blood does not appear in the fluid tube, it can be deduced that the needle is not in fluid communication with a vein or artery. Neither of these techniques has proven to be entirely satisfactory, one reason being that they both require the presence of trained hospital personnel and cannot be performed automatically.

Still another prior technique for detecting infiltrations and other fault conditions is used in a parenteral administration system that regulates flow rate using a pinch valve located in the fluid tube, between a drop chamber and the patient. In particular, the pinch valve is controllably adjusted in order to maintain the frequency of fluid drops into the drop chamber at a selected value. If the limits of the pinch valve are exceeded in attempting to maintain the selected drop frequency, it is deduced that a fault condition is present. Operator intervention is still required, however, in order to determine the particular type of fault condition, e.g., an infiltration, that is present.

A complete dislodging of the needle from the patient, such that the fluid is directed onto his skin, bedding, etc., is ordinarily detected only through a visual inspection by a hospital attendant. Such active participation by hospital personnel is not believed to be an entirely satisfactory solution to this problem.

It should be appreciated from the foregoing that there still is a need for an effective method and apparatus for automatically detecting faults such as infiltrations or an open line in a parenteral administration system of the type having an infusion device. The present invention fulfills this need.

SUMMARY OF THE INVENTION

The present invention is embodied in a fault detection apparatus, and related method, for use with a parenteral administration system of the type having an infusion device for infusing a parenteral fluid through a fluid tube and needle to a patient's vascular system. The apparatus includes pressure transducer means for monitoring the pressure of the fluid in the fluid tube and producing a corresponding pressure signal. In accordance with the invention, the apparatus further includes automatic fault detection means for qualitatively evaluating the pressure signal to determine when the fluid tube is not in proper fluid communication with the patient's vascular system, and for producing a corresponding alarm signal. This frees hospital personnel to perform other tasks without the need for repeatedly monitoring the status of the parenteral administration system.

One embodiment of the fault detection means is adapted for use with a parenteral administration system that includes a pulsing-type infusion device for administering the parenteral fluid to a patient's venous system. The fault detection means produces the alarm signal whenever it detects an infiltration of the fluid into body tissue separate from the venous system. In this embodiment, the fault detection means analyzes the pressure signal following each infusion pulse to detect impedance changes distal to the needle. Specifically, the fault detection means detects an infiltration by determining if the pressure signal ever fails to return to its steady state level within a predetermined time duration following each infusion pulse. In particular, the fault detection means high-pass filters the pressure signal and compares the filtered pressure signal with a prescribed threshold. The alarm signal is produced whenever the filtered pressure signal exceeds the threshold for longer than a prescribed time period following each infusion pulse.

Another embodiment of the fault detection means detects infiltrations whenever the infusion device is infusing fluid at a relatively high rate, e.g., 40 ml per hour. In this embodiment, the fault detection means includes pressure change means for determining if the pressure signal ever increases by more than a particular amount during a predetermined time duration. This pressure change means preferably includes means for sampling the pressure signal at spaced intervals of time, along with means for comparing the current pressure signal sample with with previous pressure signal sample, to determine if the pressure signal has increased by more than the prescribed amount during the interval between samples. The pressure change means is preferably enabled only after pressure derivative means has determined that the instantaneous rate of change of the pressure signal exceeds a prescribed level.

Two other embodiments of the fault detection means of the invention are adapted for use when the parenteral administration system administers the parenteral fluid to a patient's arterial system. In one such embodiment, the fault detection means low-pass filters the pressure signal to remove the effects of the patient's heartbeats and compares the filtered pressure signal with a predetermined threshold. An alarm signal is produced whenever the signal drops below the threshold. In another such embodiment, the fault detection means high-pass filters the pressure signal to pass only the signal components attributable to the patient's heartbeats. An alarm signal is produced whenever a dropout in the heartbeat pulses is detected.

Yet another embodiment of the fault detection means detects an open line or air bubble in the fluid tube connection between the pulsing-type infusion device and the patient. When such a condition occurs, the configuration is underdamped and the pressure signal has a ringing characteristic following each infusion pulse. The fault detection means detects this ringing by analyzing the pressure signal following each infusion pulse, to measure impedance changes distal to the needle. Specifically, the fault detection means determines, after each infusion pulse, if the ac pressure signal (i.e., high-pass filtered pressure signal) drops below a prescribed negative pressure threshold. This threshold is preferably a prescribed negative fraction of the peak positive ac pressure signal occurring immediately after each infusion pulse.

In the preferred embodiment of the apparatus, the fault detection means includes several of the embodiments described above, for detecting venous and arterial infiltrations and open lines. Appropriate switching circuitry enables operation of either the venous or the arterial infiltration circuit, depending on the use to which the system is being made. The alarm is actuated when any of the various circuits detects a fault.

Other aspects and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

FIGS. 3(a)–(f) illustrate a series of waveforms that can be present in the venous infiltration detector of FIG. 2;

FIGS. 8(a)–(c) illustrate several waveforms that can be present in the open line detector of FIG. 7.

DESCRIPTION OF THE PREFERRED EMBODIMENT

Figure 1:
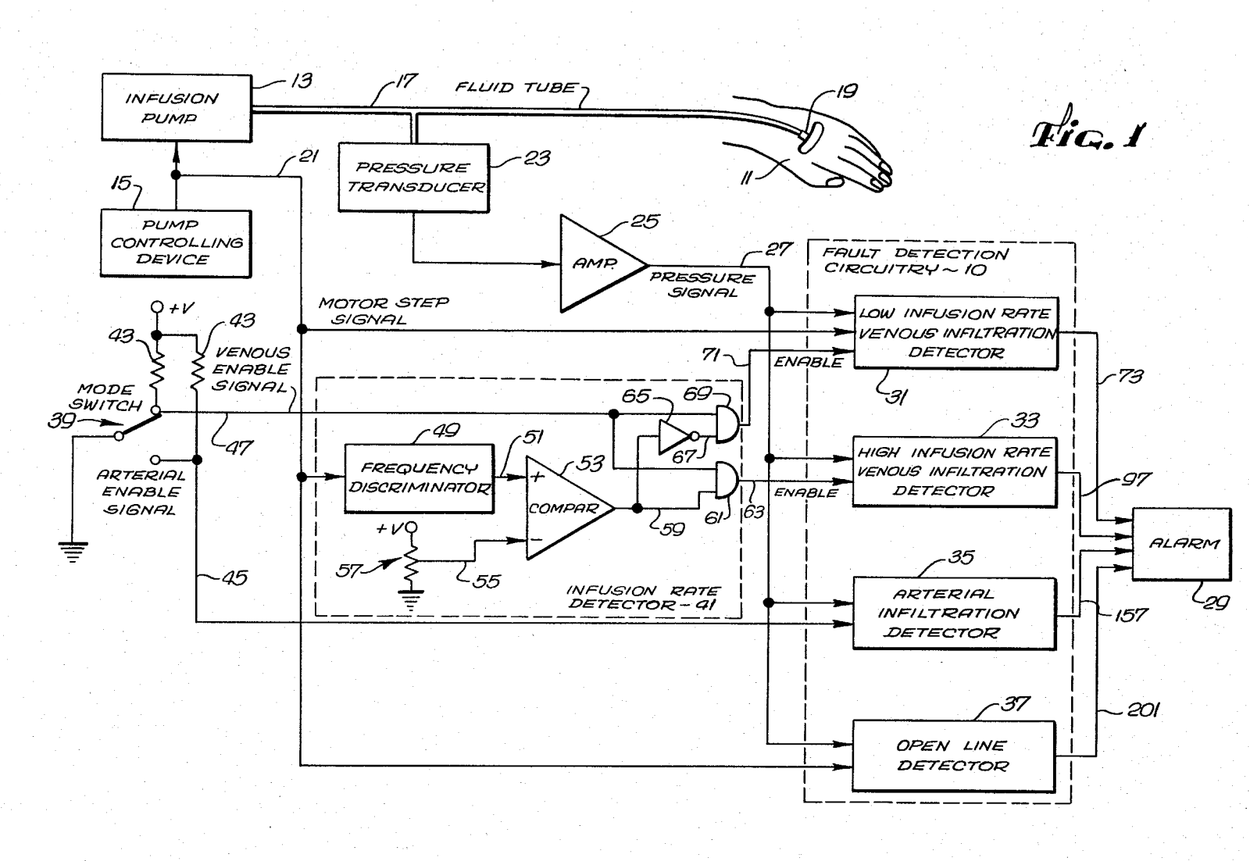
FIG. 1 is a block diagram of a parenteral administration system having circuitry for detecting venous infiltrations, arterial infiltrations and open fluid lines.

Referring now to the drawings, and particularly to FIG. 1, there is shown fault detection circuitry 10 for use in a system for administering a parenteral fluid to the vascular system of a patient 11. The system includes a conventional infusion pump 13 and associated pump controlling device 15 for pumping the parenteral fluid through a fluid tube 17 and needle 19 to the patient. The pump is preferably of the peristaltic type, which pumps the fluid in a cyclic fashion. One such suitable pump and an associated controller for controlling its speed are described in a copending and commonly-assigned application for U.S. Patent, Ser. No. 06/281,848, filed July 9, 1981, in the names of Stephen H. O'Leary et al. and entitled "Method and Apparatus for Fluid Flow Control."

The pump controlling device 15 outputs a motor step signal for coupling on line 21 to the infusion pump 13. The signal is a sequence of pulses, each of which increments the pump by one step, to infuse a predetermined volume of parenteral fluid to the patient 11.

The parenteral administration system further includes a pressure transducer 23 and an associated amplifier 25 for monitoring the fluid pressure in the fluid tube 17 and producing a corresponding pressure signal for output on line 27.

In accordance with the invention, the fault detection circuitry 10 evaluates the pressure signal on line 27 to detect certain characteristic patterns indicative of an improper fluid communication between the fluid tube 17 and the patient's vascular system. An alarm 29 is actuated if the circuitry detects such a condition. Such fault conditions include infiltrations of the fluid into body tissue other than the patient's vascular system, as well as a complete dislodging of the needle 19 from the patient 11 or a leak or air bubble in the fluid tube. In this way, a proper administration of the parenteral fluid can be ensured without the need for frequent monitoring or testing by hospital personnel.

More particularly, the fault detection circuitry 10 includes a low infusion rate venous infiltration detector 31 for detecting infiltrations when the infusion pump 13 is pumping parenteral fluid into the patient's venous system at a relatively low rate, and a high infusion rate venous infiltration detector 33 for detecting infiltrations when the pump is pumping fluid into the venous system at a relatively high rate. The fault detection circuitry further includes an arterial infiltraton detector 35 for detecting infiltrations when the pump is pumping fluid into the patient's arterial system, and an open line detector 37 for detecting when there is a leak of some kind or an air bubble in the fluid connection between the pump and the patient 11.

The system further includes a mode switch 39 for indicating whether the system is intended to administrater parenteral fluid to the patient's venous system or arterial system. The system also includes an infusion rate detector circuit 41, operable whenever the switch indicates that the system is pumping fluid into the patient's venous system to indicate whether the fluid is being pumped at a relatively high rate or a relatively low rate. The switch 39 and detector circuit 41 are used to enable operation of the appropriate venous infiltration detector circuit 31 or 33 or arterial infiltration detector circuit 35, depending on the system's operating mode.

More particularly, the mode switch 39 is a single-pole, double-throw switch having its middle terminal connected directly to ground and its two remaining terminals connected through separate resistors 43 to a positive voltage. The binary signals present on these two terminals are therefore opposite in phase to each other. One such signal is defined to be an arterial enable signal and the other is defined to be a venous enable signal.

The arterial enable signal is coupled on line 45 directly to the arterial infiltration detector circuit 35, and the venous enable signal is coupled on line 47 to the infusion rate detector 41. The infusion rate detector circuit relays the venous enable signal to either the low infusion rate venous infiltration detector 31 or the high infusion rate venous infiltration detector 33, depending on the infusion rate being effected by the infusion pump 13.

The infusion rate detector circuit 41 includes a frequency discriminator 49 for monitoring the motor step signal present on line 21 and producing an output signal having a voltage level generally proportional to the motor step signal's frequency. This output signal is coupled on line 51 to the positive input terminal of a comparator 53, which compares it with a selected reference level coupled to its negative input terminal. The reference level is supplied on line 55 from the wiper of a potentiometer 57, whose remaining two terminals are connected between ground and a positive supply voltage. If the discriminator output signal exceeds the threshold, indicating that the infusion pump 13 is pumping at a relatively high rate (e.g., above about 40 ml per hour), the comparator outputs a positive voltage level. On the other hand, if the discriminator output signal does not exceed the threshold, indicating that the pump is pumping at a relatively low rate, the comparator outputs a low voltage level signal.

The signal output by the comparator 53 is coupled on line 59 to a first AND gate 61 for ANDing with the venous enable signal supplied on line 47 from the mode switch 39. This produces a high infusion rate venous enable signal for coupling on line 63 to the high infusion rate venous infiltration detector 33. The detector 33 is thereby enabled to detect infiltrations whenever a venous infusion is selected by the mode switch and the infusion rate exceeds the prescribed threshold.

The signal output by the comparator 53 of the infusion rate detector 41 is also coupled on line 59 to a NOT gate 65, for inversion and coupling in turn on line 67 to a second AND gate 69, where it is ANDed with the same venous enable signal present on line 47. The resulting low infusion rate venous enable signal is coupled on line 71 to the low infusion rate venous infiltration detector 31. This detector 31 is thereby enabled whenever a venous infusion is selected by the mode switch 39 and the infusion rate does not exceed the prescribed threshold.

Figure 2:
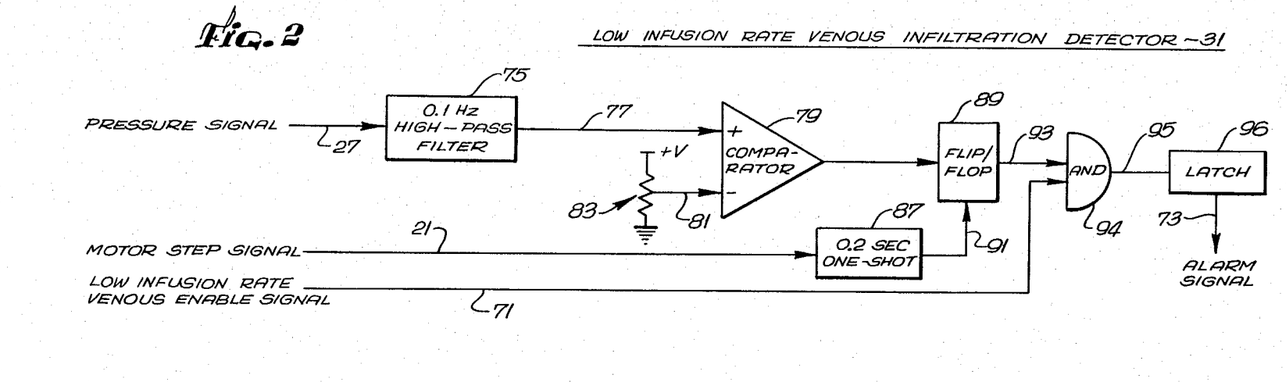
FIG. 2 is a simplified schematic diagram of a low infusion rate venous infiltration detector included in the system of FIG. 1.

Referring now to FIG. 2, there is shown a simplified schematic diagram of the low infusion rate venous infiltration detector 31. This circuit monitors the pressure signal supplied on line 27 from the amplifier 25, to detect a characteristic pattern indicative of an occlusion or infiltration of fluid into the patient's body tissue separate from his venous system. When the circuit detects such a condition, it outputs an alarm signal for coupling on line 73 to the alarm 29. Basically, the circuit determines that an occlusion or an infiltration has occurred whenever the pressure signal fails to return to its nominal value within a prescribed time duration following each of the successive pumping pulses of the infusion pump 13.

The low infusion rate venous infiltration detector 31 includes a 0.1 Hz high-pass filter 75 for filtering the pressure signal supplied on line 27, to produce a filtered pressure signal for output on line 77. The pressure signal, which is depicted in FIG. 3(c), normally includes a series of positive pressure pulses, each with an exponentially-decaying tail, as a result of the successive motor steps of the infusion pump 13.

A comparator 79 compares the filtered pressure signal with a selected positive voltage threshold supplied on line 81 from the wiper of a potentiometer 83. The other two terminals of the potentiometer are connected between ground and a positive potential. If the filtered pressure signal has a voltage level exceeding the threshold, the comparator outputs a positive signal on line 85 as shown in FIG. 3(d). The threshold is preferably selected to be about 30 percent of the pulse's peak value. Typically, the threshold is about four to six cm $H_2O$.

Figure 3:
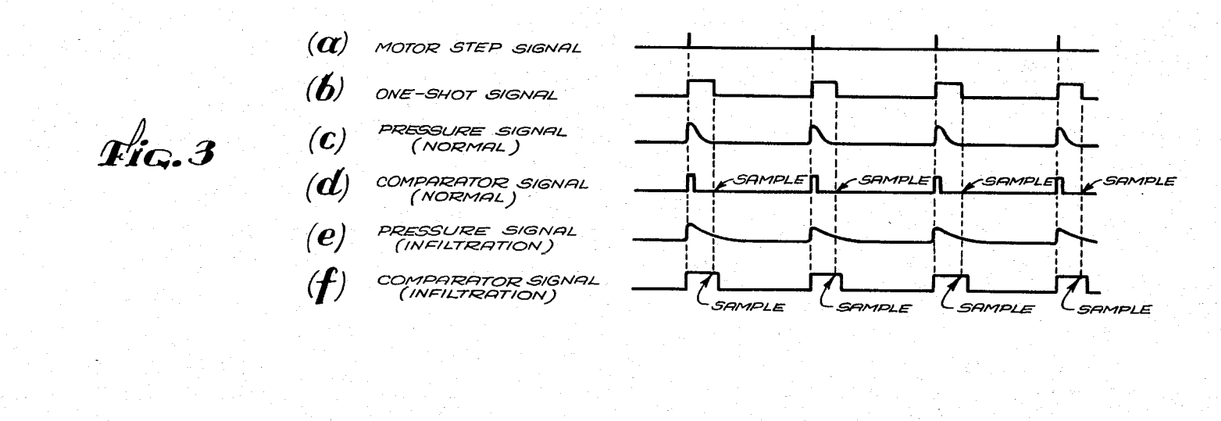

The detector 31 further includes a monostable multivibrator or one-shot 87 and a flip-flop 89 for sampling the signal output by the comparator 79 about 0.2 seconds after each pulse of the motor step signal (FIG. 3(a)). In particular, the motor step signal is supplied on line 21 to the one-shot, which produces a corresponding sequence of pulses (FIG. 3(b)), each having a duration of about 0.2 seconds. This one shot signal is coupled on line 91 to the clock input terminal of the flip-flop, which samples the pressure derivative signal at the trailing edge of each pulse. If the comparator output signal is still a positive value at this time, the flip-flop outputs a positive signal as well.

The signal output by the flip-flop 89 is coupled on line 93 to one input terminal of an AND gate 94, which ANDs the signal with the low infusion rate venous enable signal supplied on line 71. It will be recalled that this enable signal indicates that the parenteral administration system is intended to be administering fluid to the patient's venous system at a relatively low rate. If both inputs to the AND gate are a positive value, it is deduced that an infiltration is occurring and the AND gate outputs a trigger signal for coupling on line 95 to a latch 96, which, in turn, produces an alarm signal for coupling on line 73 to the alarm 29 (FIG. 1).

During normal situations, when the needle 19 is properly inserted into the patient's vein, the pressure signal (FIG. 3(c)) returns to its nominal value relatively quickly after each pulse of the motor step signal (FIG. 3(a)). As a result, the pressure signal does not exceed the threshold and the comparator output signal (FIG. 3(d)) is at a low level at the successive sample times. The detector circuit 31 therefore does not produce an alarm signal.

On the other hand, during abnormal situations, when the needle 19 is not in proper communication with the patient's venous system and an infiltration is occurring, the pressure signal (FIG. 3(e)) has a relatively long decay time. This apparently occurs because of an inability of the body tissue to dissipate rapidly each infusion of parenteral fluid. Because of the long decay time, the comparator output signal (FIG. 3(f)) is still at a high level at the time it is sampled by the flip-flop 89. An alarm signal is therefore produced on line 73.

Figure 4:
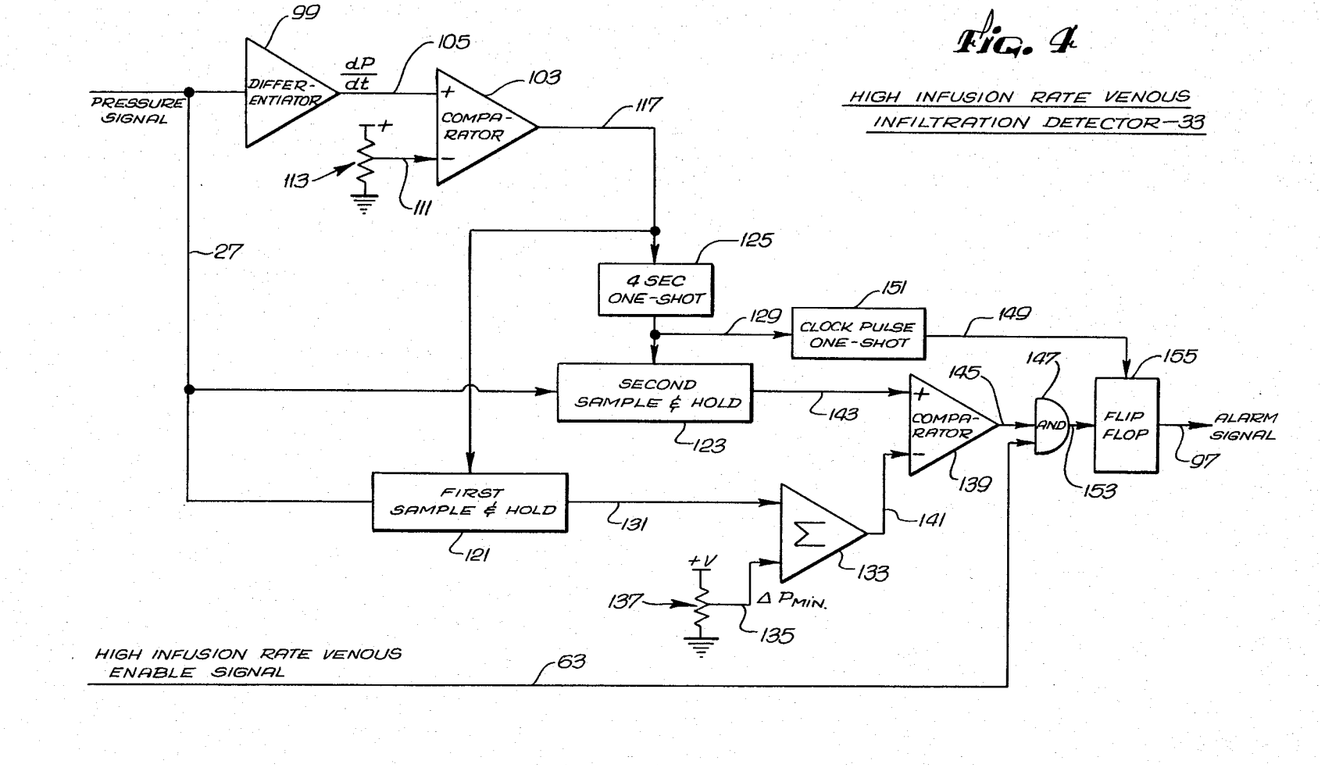
FIG. 4 is a simplified schematic diagram of a high infusion rate venous infiltration detector included in the system of FIG. 1.

Referring now to FIG. 4, there is shown a simplified schematic diagram of the high infusion rate venous infiltration detector 33 of FIG. 1. Basically, this circuit monitors the pressure signal supplied on line 27 to determine if the pressure in the fluid tube 17 ever increases by more than a selected amount during a predetermined time period. It makes this determination only after the instantaneous rate of change of pressure first exceeds a prescribed level, e.g., 30 cm $H_2O$ per second. A positive pressure slope less than this lower threshold can occur during normal situations. A positive pressure slope greater than about 250 cm $H_2O$ per second can indicate a downstream occlusion, but is treated by the detector circuit as though it were an infiltration. When the instantaneous rate of change of the pressure signal first exceeds the 30 cm $H_2O$ per second threshold, the detector circuit samples the pressure signal immediately and again approximately four seconds later. If the second sample exceeds the first by more than a prescribed amount, e.g., 75 cm $H_2O$ it is deduced that an infiltration is occurring. An alarm signal is then output on line 97 for coupling to the alarm 29 (FIG. 1).

The detector circuit 33 of FIG. 4 is suitable for use in detecting infiltrations when the parenteral administration system is administering fluids at rates above about 40 ml per hour. The low infusion rate venous infiltration detector 31 of FIG. 2 could also function properly at such infusion rates, but would ordinarily require the momentary disabling of the infusion pump 13 each time it seeks to detect an infiltration. This is because the successive pulses of the infusion pump would then be occurring less than 0.2 seconds apart, which is the nominal sample delay time required by the circuit.

The high infusion rate venous infiltration detector 33 includes a differentiator 99 for producing a pressure derivative signal, along with a comparator 103 for comparing the pressure derivative signal with a threshold corresponding to 30 cm $H_2O$ per second. The pressure signal is input to the differentiator on line 27, and the pressure derivative signal is output by the differentiator on line 105 for coupling to the comparator's positive input terminal. The comparator's negative input terminal is coupled on line 111 to the wiper of a potentiometer 113. The remaining two terminals of the potentiometer are connected to ground and a positive supply voltage, so the voltage present at the wiper of the potentiometer represents a selected positive voltage threshold. The comparator produces a positive-valued trigger signal whenever the pressure derivative signal exceeds the threshold.

The detector circuit 33 of FIG. 4 further includes first and second sample and hold circuits 121 and 123 and a four second monostable multivibrator or one-shot 125. The trigger signal produced by the comparator 103 is coupled on line 117 to both the first sample and hold circuit and the one-shot. Whenever the trigger signal goes into a high state, indicating that the instantaneous pressure derivative signal has just exceeded the rate of change threshold, the first sample and hold circuit samples the pressure signal supplied on line 27 and the one-shot simultaneously initiates a four second output pulse that is in a low state. The one-shot output signal is coupled on line 129 to the second sample and hold circuit, whereupon four seconds later it like-wise samples the pressure signal.

The signal output by the first sample and hold circuit 121 is coupled on line 131 to a summer 133, for summing with a selected positive voltage level supplied on line 135 from a potentiometer 137. This voltage level represents the minimum amount by which the pressure signal must increase during a four second period for an infiltration to be detected. A comparator 139 compares the summer output signal with the signal output by the second sample and hold circuit 123. In particular, the summer output signal is coupled on line 141 to the comparator's negative input terminal, and the second sample and hold circuit output signal is coupled on line 143 to the comparator's positive input terminal. If the sample and hold signal exceeds the summer signal, it is deduced that the pressure in the fluid tube 17 has increased by more than the prescribed amount (75 cm $H_2O$) during the preceeding four second period and that an infiltration has therefore occured.

The signal output by the comparator 139 is coupled on line 145 to an AND gate 147, for ANDing with the high infusion rate venous enable signal supplied on line 63 from the infusion rate detector circuit 41 (FIG. 1). If both AND gate input signals are high, the AND gate produces a high signal for coupling on line 153 to the data input terminal of a flip-flop 155. A clock pulse signal for clocking the flip-flop occurs shortly after the end of the four second period, at which time the comparator and AND gate output signals have stabilized. This clock pulse signal, which is coupled to the flip-flop's clock terminal on line 149, is produced by a clock pulse one-shot 151 in response to the one-shot pulse supplied on line 129 from the four second one-shot 125. The flip-flop in turn produces the alarm signal for output on line 97.

Figure 5:
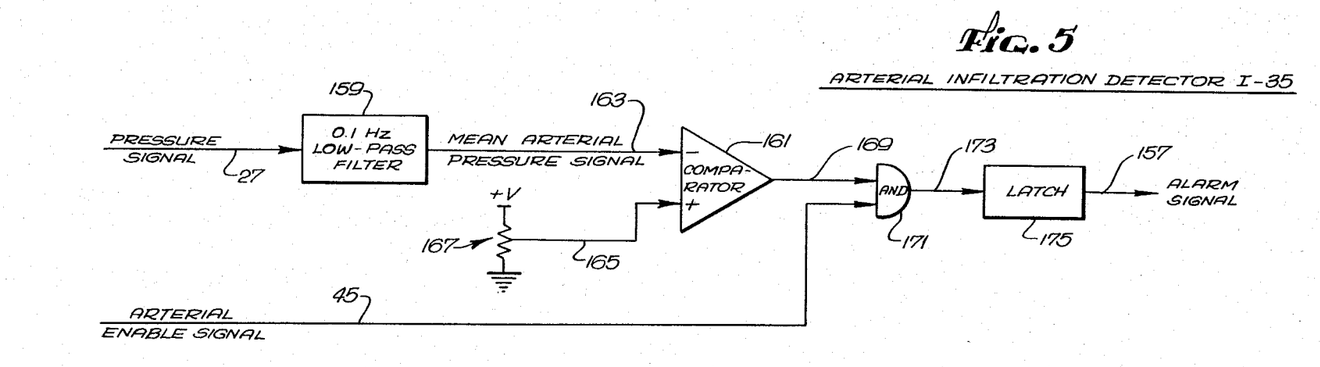
FIG. 5 is a simplified schematic diagram of one embodiment of an arterial infiltration detector suitable for use in the system of FIG. 1.

Referring now to FIG. 5, there is shown a simplified schematic diagram of one embodiment of the arterial infiltration detector 35 of FIG. 1. Basically, the circuit compares the mean pressure signal, which should correspond to the patient's mean arterial pressure, to a prescribed positive threshold, preferably about 60 cm of water, and outputs an alarm signal on line 157 whenever the signal drops below the threshold.

More particularly, the arterial infiltration detector 35 of FIG. 5 includes a 0.1 Hz low-pass filter 159 and a comparator 161. The filter filters the pressure signal supplied on line 27 to produce a mean arterial pressure signal for coupling on line 163 to the comparator's negative input terminal. The prescribed positive threshold is coupled to the comparator's positive input terminal on line 165 from the wiper of a potentiometer 167. During normal operation, when the needle 19 is properly inserted in the patient's artery, the mean arterial pressure signal will exceed the threshold selected by the potentiometer and the comparator will output a signal having a negative level. Conversely, when the needle is not properly inserted in the patient's artery and an infiltration is occurring, the mean arterial pressure signal will not exceed the threshold and the comparator will output a signal having a positive level. A bandwidth of about 0.1 Hz is preferred for the low-pass filter, to substantially remove the effects of the patient's heartbeats.

The signal output by the comparator 161 is coupled on line 169 to an AND gate 171, for ANDing with the arterial enable signal supplied on line 45. If both signals are at a positive level, then the AND gate likewise outputs a positive level signal. This AND gate output signal is coupled on line 173 to a latch 175, which produces the alarm signal for output on line 157.

Figure 6:
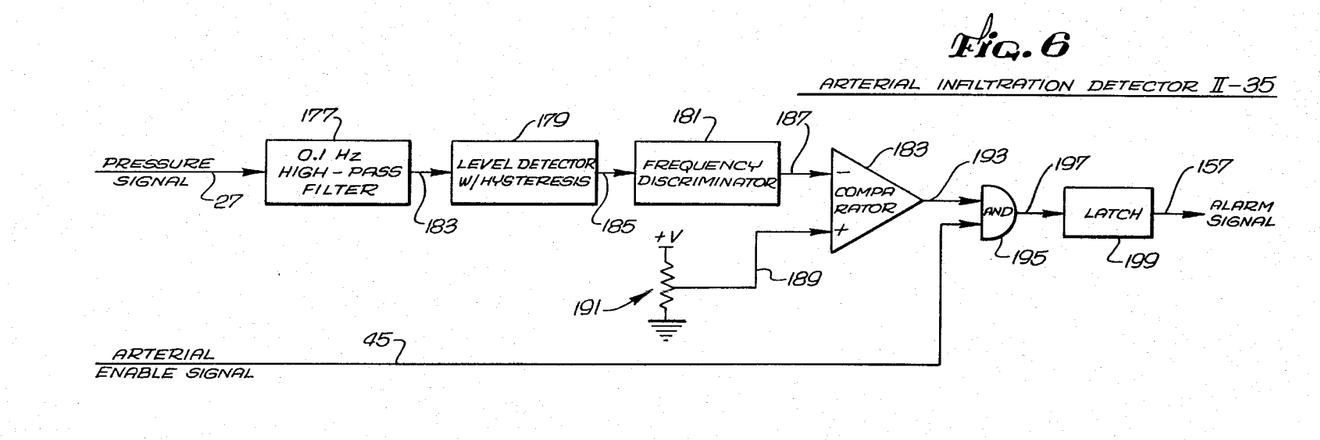
FIG. 6 is a simplified schematic diagram of an alternative arterial infiltration detector suitable for use in the system of FIG. 1.

With reference now to FIG. 6, there is shown a simplified schematic diagram of an alternative embodiment of the arterial infiltration detector 35 of FIG. 1. In this embodiment, infiltrations into the patient's body tissue separate from his arterial system are detected by monitoring the pressure signal to detect dropouts in the pressure variations caused by the patient's heartbeat.

More particularly, the arterial infiltration detector 35 of FIG. 6 includes a 0.1 Hz high-pass filter 177, a level detector with hysteresis 179, a frequency discriminator 181 and a comparator 183. The high-pass filter filters the pressure signal supplied on line 27 to remove its dc level and pass only the successive pulses representative of the patient's heartbeats. The heartbeat pulses are present in the pressure signal whenever the fluid tube 17 and the needle 19 (FIG. 1) are coupled directly to the patient's arterial system. The high-pass filtered signal is coupled on line 185 to the level detector, which converts the signal to a corresponding pulse sequence signal. The level detector detects only pulses having a magnitude of at least about 15 cm H₂O. The pulse sequence produced by the level detector is coupled on line 185 to the frequency discriminator, which produces an output signal having a level proportional to the frequency of its input signal.

Thus, if the needle 19 is properly inserted into the patient's arterial system, the heartbeats will be represented in the pressure signal and the frequency discriminator 181 will output a relatively high voltage level signal. On the other hand, if the needle is not properly inserted into the patient's arterial system, the heartbeats will not be represented in the pressure signal and the frequency discriminator will output a relatively low level signal.

The discriminator output signal is coupled on line 187 to the negative input terminal of the comparator 183, which compares it with a selected positive reference level supplied to its positive input terminal on line 189 from a potentiometer 191. Thus, if the frequency discriminator output signal ever drops below the reference level, the comparator outputs a positive voltage level. The reference level preferably corresponds to a pulse frequency of about 15 beats per minute.

The signal output by the comparator 183 is coupled on line 193 to an AND gate 195, where it is ANDed with the arterial enable signal supplied on line 45. If both signals are at a positive level, it is deduced that an arterial infiltration has occurred and the AND gate outputs a corresponding signal for coupling on line 197 to a latch 199. The latch, in turn, outputs the alarm signal for coupling on line 157 to the alarm 29 (FIG. 1).

Figure 7:
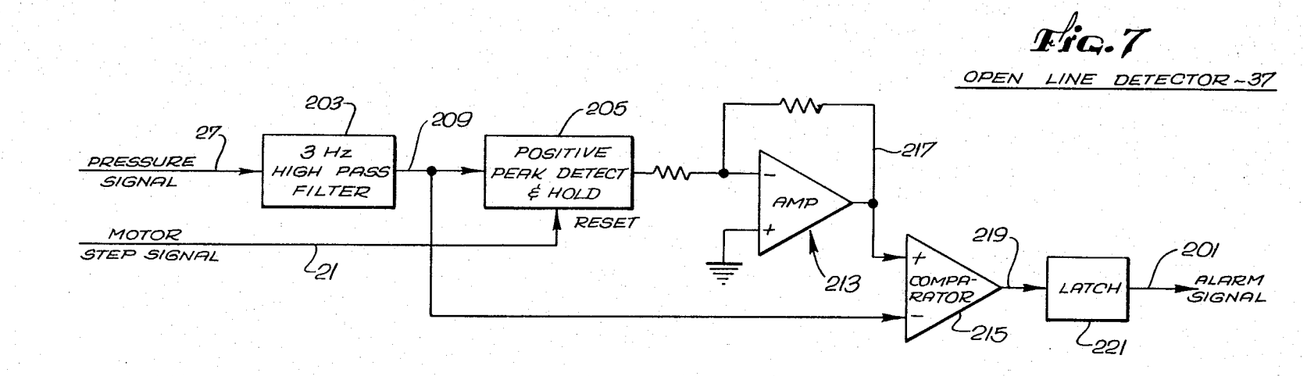
FIG. 7 is a simplified schematic diagram of an open line detector included in the system of FIG. 1.

A simplified schematic diagram of the open line detector circuit 37 is depicted in FIG. 7. This circuit monitors the pressure signal supplied on line 27 to detect a fluid leakage, i.e., an open line or an air bubble in the fluid tube 17 between the infusion pump 13 and the patient 11. If the circuit detects such a condition, it outputs an alarm signal for coupling on line 201 to the alarm 29.

Figure 8:
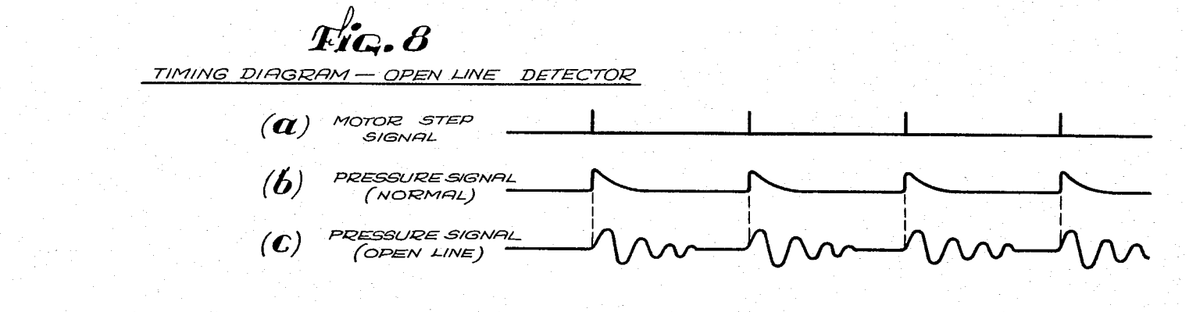

During normal operation, when the needle 19 is properly inserted into the patient's vein or artery, the pressure signal (FIG. 8(b)) reflects an overdamped or critically damped condition. The signal includes a positive pressure pulse immediately following each pulse of the motor step signal (FIG. 8(a)), with each pulse having an exponentially-decaying tail as the patient's vein or artery carries away the small volume of fluid being infused. Conversely, when an open line condition is present, the pressure signal (FIG. 8(c)) reflects an underdamped condition. Each pulse of the motor step signal results in an initial increase in fluid pressure, followed immediately thereafter by a momentary decrease in pressure to a level less than the level before the pulse occurred.

Basically, the open line detector 37 detects the occurrence of an open line condition by detecting an underdamped characteristic in the pressure signal, i.e., an overshoot or ringing in the pressure signal following each pulse of the motor step signal. More particularly, the open line detector includes a 3 Hz high-pass filter 203 and a positive peak detector and hold circuit 205. The high-pass filter filters the pressure signal supplied on line 27, to remove its dc level but pass the frequencies associated with the successive steps of the infusion pump 13. The filtered signal is coupled on line 209 to the peak detector and hold circuit, which outputs a level equal to the signal's positive peak. The peak detector circuit, which is reset by each pulse in the motor step signal supplied on line 21, can include for example, a series-connected diode followed by a capacitor to ground.

The signal output by the positive peak detector and hold circuit 205 is coupled on line 211 to an amplifier 213 for amplification by a prescribed fractional amount, e.g., negative two-thirds. This amplified signal serves as a threshold to which the high-pass filtered pressure signal is compared in a comparator 215. If the filtered signal is ever more negative than the threshold, it is deduced that there is substantial ringing occuring in the pressure signal and that an open line condition is therefore present.

More particularly, the signal output by the amplifier 213 is coupled on line 217 to the comparator's positive input terminal and the high-pass filtered pressure signal is coupled on line 209 to the comparator's negative input terminal. The resulting comparator output signal is coupled on line 219 to a latch 221, which produces the alarm signal for coupling on line 201 to the alarm 29.

The alarm 29 is responsive to any of the four alarm signals coupled to it on lines 73, 97, 157 and 201 from the fault detection circuitry 10. It includes a four-input OR gate that OR's together the four signals and actuates a visual or audible indicator whenever any of the signals is high. It further includes a switch for use in selectively clearing the latches or flip-flops at the output stage of each detector in the fault detection circuitry.

It should be appreciated from the foregoing description that the present invention provides an improved apparatus and related method for detecting fault conditions such as an infiltration or an open line in a parenteral administration system. The apparatus is particularly adapted for use with a system of the type that includes a pulsing infusion pump for incrementally pumping a parenteral fluid through a fluid tube and needle to a patient's vascular system. The apparatus monitors the pressure in the fluid tube to detect characteristic patterns indicative of infiltrations of the fluid into the patient's body tissue separate from either his venous system or arterial system, as well as an open line or air bubble in the fluid coupling between the infusion pump and the patient.

It should also be appreciated that the fault detection circuitry 10 and the infusion rate detector 41 described above can be implemented in both hardware and software.

Although the present invention has been described in detail with reference to the presently preferred embodiments, it should be understood by those of ordinary skill in the art that various alternatives, modifications and equivalents can be constructed without departing from the invention. Accordingly, the invention is limited only by the following claims.

I claim:

1. Fault detection apparatus for use with a parenteral administration system having an infusion device for infusing parenteral fluid through a fluid tube to the vascular system of a patient, comprising:
   pressure transducer means for monitoring the pressure of the fluid in the fluid tube and producing a corresponding pressure signal;
   fault detection means for evaluating the pressure signal over a period of time to detect characteristic patterns in the waveform of the pressure signal evaluated which are indicative of improper fluid communication between the fluid tube and the vascular system of the patient; and
   means for producing a corresponding alarm signal whenever the fault detection means detects such a characteristic pattern.

2. Fault detection apparatus as defined in claim 1, wherein:
   the infusion device infuses the parenteral fluid to the venous system of the patient in a pulsing fashion; and
   the fault detection means detects an infiltration of the parenteral fluid into body tissue separate from the venous system by determining if the pressure signal does not return to a steady state level within a prescribed time duration following an infusion pulse.

3. Fault detection apparatus as defined in claim 1, wherein the fault detection means includes:
   means for high-pass filtering the pressure signal to produce a filtered pressure signal; and
   means for comparing the filtered pressure signal with a prescribed threshold signal and for producing the alarm signal whenever the filtered pressure signal exceeds the threshold signal for a prescribed time duration following each infusion pulse.

4. Fault detection apparatus as defined in claim 1, wherein the fault detection means includes pressure change sensing means for detecting if the pressure signal ever increases by more than a predetermined amount during a predetermined time duration and for producing the alarm signal whenver the pressure signal increases by more than a predetermined amount during a predetermined time duration.

5. Fault detection apparatus as defined in claim 4, wherein teh fault detection means further includes means for enabling the pressure change sensing means only when the rate of change of the pressure signal exceeds a prescribed level.

6. Fault detection apparatus as defined in claim 6, wherein the pressure change sensing means includes:
   means for sampling the pressure signal at spaced intervals of time; and
   means for comparing the current pressure signal with the previous pressure signal to determine if the pressure signal has increased by more than the predetermined amount during the interval between signals.

7. Fault detection apparatus as defined in claim 1, wherein:
   the parenteral administration system is arranged to administer the parenteral fluid to the arterial system of the patient; and
   the fault detection means which detects an infiltration of the parenteral fluid into body tissue separate from the arterial system includes
   means for low-pass filtering the pressure signal to produce a filtering pressure signal; and
   means for comparing if the filtered pressure signal with a predetermined threshold signal and producing the alarm signal whenever the filtered signal drops below the threshold signal.

8. Fault detection apparatus as defined in claim 7, wherein the fault detection means includes:
   means for low-pass filtering the pressure signal to produce a mean pressure signal; and
   means for comparing if the mean pressure signal with a predetermined threshold and producing the alarm signal whenever the signal drops below the threshold.

9. Fault detection apparatus as defined in claim 8, wherein the fault detection means includes:
   means for high-pass filtering the pressure signal to produce a variable pressure signal; and
   means for evaluating the variable pressure signal to detect a dropout in variable signal components attributable to the patient's heartbeats and for producing the alarm signal whenever such an occurrence is detected.

10. Fault detection apparatus as defined in claim 9, wherein:
    the infusion device infuses the parenteral fluid to the vascular system of the patient in a pulsing fashion;
    the fault detection means detects a disconnection of the fluid tube or an air bubble in the fluid tube between the infusion device and the patient; and
    the fault detection means includes
    means for high-pass filtering the pressure signal to produce a variable pressure signal, and
    means for comparing the variable pressure signal with a predetermined threshold signal, a disconnection in the fluid tube or an air bubble in the fluid tube being detected whenever the variable pressure signal is less than the threshold following each infusion pulse.

11. Infiltration detection apparatus for use with a parenteral administration system having a pulsing infusion device for incrementally infusing a parenteral fluid through a fluid tube to the venous system of a patient, comprising:
    pressure transducer means for monitoring the pressure of the fluid in the fluid tube and producing a corresponding pressure signal; and
    infiltration detection means for evaluating the pressure signal over a period of time to detect a characteristic pattern in the waveform of the pressure signal evaluated wherein the pressure signal fails to return substantially to a steady state level within a predetermined time period following an infusion pulse, and producing an infiltration alarm signal whenever such an occurrence is detected.

12. Infiltration detection apparatus as defined in claim 11, wherein:
    the infiltration detection means includes
    means for high-pass filtering the pressure signal to produce a filtered pressure signal, and comparator means for comparing the filtered pressure signal with a prescribed positive threshold signal; and the infiltration detection means produces the infiltration alarm signal whenever the comparator means determines that the filtered pressure signal remains higher than the threshold signal for longer than the predetermined time period.

13. Infiltration detection apparatus as defined in claim 12, wherein the infiltration detection means further includes means for sampling the comparator means after the predetermined time period following each infusion pulse.

14. Infiltration detection apparatus as defined in claim 11, wherein the predetermined time period is about 0.2 seconds.

15. Infiltration detection apparatus for use with a parenteral administration system having an infusion device for infusing a parenteral fluid through a fluid tube to the venous system of a patient, comprising:

pressure transducer means for monitoring the pressure of the fluid in the fluid tube and producing a corresponding pressure signal; and infiltration detection means for evaluating the pressure signal over a period of time to detect a characteristic pattern in the waveform of the pressure signal evaluated wherein the pressure signal increases by more than a predetermined amount during a predetermined time period and producing an infiltration alarm signal whenever such an ocurrence is detected.

16. Infiltration detection apparatus as defined in claim 15, wherein:

the fault detection means includes means for differentiating the pressure signal to produce a pressure derivative signal representative of the rate of change of the pressure signal, and comparator means for comparing the pressure derivative signal with a prescribed threshold signal and producing a trigger signal whenever the pressure derivative signal first exceeds the threshold signal; and the fault detection means evaluates the pressure signal to produce the alarm signal only when the comparator means produces the trigger signal.

17. Infiltration detection apparatus as defined in claim 16, wherein the fault detection means further includes:

first sampling means for sampling the pressure signal immediately after the comparator means produces the trigger signal, to produce a first signal;

second sampling means for sampling the pressure signal the prescribed time period after the comparator means produces the trigger signal, to produce a second signal;

means for comparing the first signal with the second signal and for producing the alarm signal whenever the second signal exceeds the first signal by more than a predetermined amount.

18. Infiltration detection apparatus for use with a parenteral administration system having an infusion device for infusing a parenteral fluid through a fluid tube to the arterial system of a patient, comprising:

pressure transducer means for monitoring the pressure of the fluid in the fluid tube and producing a corresponding pressure signal; and infiltration detection means for evaluating the pressure signal over a period of time to detect a characteristic pattern in the waveform of the pressure signal evaluated wherein the mean value of the pressure signal drops below a predetermined threshold value and for producing an infiltration alarm signal whenever such an occurrence is detected.

19. Infiltration detection apparatus as defined in claim 18, wherein the infiltration detection means includes:

filter means for low-pass filtering the pressure signal to remove signal components attributable to the patient's heartbeats; and comparator means for comparing the filtered pressure signal with a prescribed threshold signal and producing the alarm signal whenever the filtered pressure signal drops below the threshold signal.

20. Infiltration detection apparatus for use with a parenteral administration system having an infusion device for infusing a parenteral fluid through a fluid tube to the arterial system of a patient, comprising:

pressure transducer means for monitoring the pressure of the fluid in the fluid tube and producing a corresponding pressure signal; and infiltration detection means for evaluating the pressure signal to detect a dropout in signal components attributable to the patient's heartbeats and for producing an infiltration alarm signal whenever such an occurrence is detected.

21. Infiltration detection apparatus as defined in claim 20, wherein the infiltration detection means includes:

filter means for high-pass filtering the pressure signal to pass only the variable signal components representing heartbeat signal components; and heartbeat detection means for detecting a dropout of the heartbeat signal components in the filtered presssure signal and producing the alarm signal whenever such an occurrence is detected.

22. Infiltration detection apparatus as defined in claim 21, wherein the heartbeat detection means includes:

pulse detector means for detecting pulses in the filtered pressure signal and producing a corresponding pulse sequence signal; and comparator means for comparing the frequency of the pulse sequence signal with a predetermined frequency threshold signal and for producing the alarm signal whenever the pulse frequency drops below the threshold signal.

23. Infiltration detection apparatus as defined in claim 22, wherein the pulse detector means detects only pulses in the filtered pressure signal having magnitudes corresponding to at least about 15 centimeters of water.

24. Open line detection apparatus for use with a parenteral administration system having a pulsing infusion device for incrementally infusing a parenteral fluid through a fluid tube to the vascular system of a patient, comprising:

pressure transducer means for monitoring the pressure of the fluid in the fluid tube and producing a corresponding pressure signal; and open line detection means for detecting an underdamped characteristic in the pressure signal following each infusion pulse of the infusion device, such an underdamped characteristic indicating an open fluid line or an air bubble in the fluid line, the detection means producing an open line alarm signal when it detects such a characteristic.

25. Open line detection apparatus as defined in claim 24, wherein the open line detection means includes:

means for high-pass filtering the pressure signal to pass only its variable signal components; and comparator means for comparing the filtered pressure signal with a prescribed negative threshold signal following each infusion pulse of the infusion device and for producing the alarm signal whenever the filtered pressure signal is more negative than the threshold signal.

26. Open line detection apparatus as defined in claim 25, wherein the negative threshold signal compared by the comparator means is a prescribed negative fraction of the peak positive value of the filtered pressure signal following each infusion pulse of the infusion device.

27. Open line detection apparatus as defined in claim 26, wherein the comparator means includes:

positive peak detector and hold means for monitoring the filtered pressure signal and producing a peak positive signal indicative of the peak positive value thereof following each infusion pulse of the infusion device;

amplifier means for amplifying the peak positive signal by a prescribed negative fraction to produce the negative threshold signal; and means for comparing the filtered pressure signal with the negative threshold signal and for producing the alarm signal whenever the signal is more negative than the threshold signal.

28. Open line detection apparatus as defined in claim 27, wherein the negative fraction used in the amplifier means is about negative two-thirds.

29. A parenteral administration system for infusing a parenteral fluid into the vascular system of a patient, comprising:

an infusion device;

a fluid coupled between the infusion device and the vascular system of a patient, such that the device can infuse a parenteral fluid into the vascular system;

pressure transducer means for monitoring the pressure of the fluid in the fluid tube and producing a corresponding pressure signal; and fault detection means for evaluating the pressure signal over a period of time to detect characteristic patterns in the waveform of the pressure signal evaluated which are indicative of improper communication between the fluid tube and the patient's vascular system; and means for producing a corresponding alarm signal whenever the fault detection means detects such a characteristic signal pattern.

30. A parenteral administration system as defined in claim 29, wherein:

the infusion device infuses the parenteral fluid in a pulsing fashion, each infusion pulse infusing a predetermined volume of fluid;

the fluid tube couples the infusion device to the patient's venous system; and the fault detection means detects an infiltration of parenteral fluid into body tissue separate from the patient's venous system by determining if the pressure signal after increasing fails to return to a steady state level within a predetermined time period following an infusion pulse.

31. A parenteral administration system as defined in claim 29, wherein:

the fluid tube couples the infusion device to the patient's venous system;

the fault detection means detects an infiltration of parenteral fluid into body tissue separate from the patient's venous system; and the fault detection means includes means for differentiating the pressure signal to produce a pressure derivative signal representative of the rate of change of the pressure signal, comparator means for determining if the pressure derivative signal exceeds a predetermined level and for producing a corresponding trigger signal, and means for detecting if the pressure signal increases by more than a predetermined amount within a predetermined time period following initiation of the trigger signal and for producing the alarm signal whenever such an occurrence is detected.

32. A parenteral administration system as defined in claim 29, wherein:

the fluid tube couples the infusion device to the patient's arterial system;

the fault detection means detects an infiltration of parenteral fluid into body tissue separate from the patient's arterial system; and the fault detection means includes means for low-pass filtering the pressure signal to produce a filtered pressure signal, and means for comparing the filtered pressure signal with a predetermined threshold signal and for producing the alram signal if the filtered pressure signal ever drops below the threshold signal.

33. A parenteral administration system as defined in claim 29, wherein:

the fluid tube couples the infusion device to the patient's arterial system;

the fault detection means detects an infiltration of parenteral fluid into body tissue separate from the patient's arterial system; and the fault detection means includes means for high-pass filtering the pressure signal to produce a variable pressure signal, and means for evaluating the variable pressure signal to detect a dropout in signal components attributable to the patient's heartbeats and for producing the alarm signal whenever such an occurrence is detected.

34. A parenteral administration system as defined in claim 29, wherein:

the infusion device infuses the parenteral fluid in a pulsing fashion; and the fault detection means determines that the fluid tube is disconnected from the patient or that an air bubble is present in the fluid tube by detecting an underdamped characteristic in the pressure signal following each infusion pulse of the infusion device, the fault detection means producing the alarm signal whenever it detects such an underdamped characteristic.

35. A method for detecting fluid infiltrations suitable for use in a parenteral administration system having a pulsing infusion device for incrementally infusing a parenteral fluid through a fluid tube to the venous system of a patient, comprising steps of:

monitoring the pressure of the fluid in the fluid tube and producing a corresponding pressure signal; and evaluating the pressure signal over a period of time to detect if the signal fails to return substantially to a steady state level within a predetermined time period following an infusion pulse, and producing an infiltration alarm signal whenever such an occurrence is detected.

36. A method for detecting fluid infiltrations as defined in claim 35, wherein:
the step of evaluating includes steps of
high-pass filtering the pressure signal to produce a filtered pressure signal, and
comparing the filtered pressure signal with a prescribed threshold signal; and
the step of evaluating produces the infiltration alarm signal whenever the step of comparing determines that the filtered pressure signal exceeds the threshold signal for longer than the predetermined time period.

37. A method for detecting fluid infiltrations as defined in claim 36, wherein the step of comparing is performed only at the end of the predetermined time period following each infusion pulse.

38. A method for detecting fluid infiltrations as defined in claim 35, wherein the predetermined time period considered in the step of evaluating is about 0.2 seconds.

39. A method for detecting fluid infiltrations for use in a parenteral administration system having an infusion device for infusing a parenteral fluid through a fluid tube to the venous system of a patient, comprising steps of:
monitoring the pressure of the fluid in the fluid tube and producing a corresponding pressure signal; and
evaluating the pressure signal over a period of time to detect a characteristic pattern in the waveform of the pressure signal evaluated wherein the pressure signal increases by more than a predetermined amount during a predetermined time period, and producing an infiltration alarm signal whenever such an occurrence is detected.

40. A method for detecting fluid infiltrations as defined in claim 39, wherein:
the step of evaluating includes steps of
differentiating the pressure signal to produce a pressure derivative signal representing the rate of change of the pressure signal, and
comparing the pressure derivative signal with a prescribed threshold signal and producing a trigger signal whenever the pressure derivative signal first exceeds the threshold signal; and
the step of evaluating produces the alarm signal only when the step of comparing produces the trigger signal.

41. A method for detecting fluid infiltrations as defined in claim 40, wherein the step of evaluating further includes steps of:
sampling the pressure signal immediately after the step of comparing produces the trigger signal, to produce a first signal;
sampling the pressure signal a prescribed time period after the step of comparing produces the trigger signal, to produce a second signal;
comparing the first signal with the second signal and producing the alarm signal whenever the second signal exceeds the first signal by more than a predetermined amount.

42. A method for detecting fluid infiltrations for use in a parenteral administration system having an infusion device for infusing a parenteral fluid through a fluid tube to the arterial system of a patient, comprising steps of:
monitoring the pressure of the fluid in the fluid tube and producing a corresponding pressure signal; and
evaluating the pressure signal over a period of time to detect a characteristic pattern in the waveform of the pressure signal evaluated wherein the mean value of the pressure signal drops below a predetermined threshold, and producing an infiltration alarm signal whenever such an occurrence is detected.

43. A method for detecting fluid infiltrations as defined in claim 42, wherein the step of evaluating includes steps of:
low-pass filtering the pressure signal to remove variable signal components attributable to the patient's heartbeats; and
comparing the filtered pressure signal with a prescribed threshold signal, and producing the alarm signal whenever the filtered pressure signal drops below the threshold signal.

44. A method for detecting fluid infiltrations for use in a parenteral administration system having an infusion device for infusing a parenteral fluid through a fluid tube to the arterial system of a patient, comprising steps of:
monitoring the pressure of the fluid in the fluid tube and producing a corresponding pressure signal; and
evaluating the pressure signal over a period of time to detect a characteristic pattern in the waveform of the pressure signal evaluated wherein an indicative decrease occurs in variable signal components attributable to the patient's heartbeats drop below a predetermined limit, and producing an infiltration alarm signal whenever such an occurrence is detected.

45. A method for detecting fluid infiltrations as defined in claim 44, wherein the step of evaluating includes steps of:
high-pass filtering the pressure signal to pass only variable signal components attributable to its heartbeat; and
detecting a dropout of the heartbeat signal components in the filtered pressure signal, and producing the alarm signal whenever such an occurrence is detected.

46. A method for detecting fluid infiltrations as defined in claim 45, wherein the step of detecting a dropout includes steps of:
detecting pulses in the filtered pressure signal, and producing a corresponding pulse sequence signal; and
comparing the frequency of the pulse sequence signal with a predetermined frequency threshold, and producing the alarm signal whenever the pulse frequency drops below the threshold.

47. A method for detecting fluid infiltrations as defined in claim 40, wherein the step of detecting pulses detects only pulses in the filtered pressure signal having magnitudes corresponding to at least about 15 centimeters of water.

48. A method for detecting an open fluid line suitable for use in a parenteral administration system having a pulsing infusion device for incrementally infusing a parenteral fluid through a fluid tube to the vascular system of a patient, comprising steps of:
monitoring the pressure of the fluid in the fluid tube and producing a corresponding pressure signal;
detecting an underdamped characteristic in the pressure signal following each infusion pulse for the infusion device, such an underdamped characteristic indicating an open fluid line or an air bubble in the fluid line; and producing an open line alarm signal whenever the step of detecting detects such an underdamped characteristic.

49. A method for detecting an open fluid line as defined in claim 48, wherein:

the step of detecting includes steps of
high-pass filtering the pressure signal to pass only variable signal components thereof, and
comparing the filtered pressure signal with a prescribed threshold signal following each infusion pulse of the infusion device; and the step of producing produces the alarm signal whenever the filtered pressure signal is less than the threshold signal.

50. A method for detecting an open fluid line as defined in claim 49, wherein the negative threshold compared in the step of comparing is a prescribed negative fraction of the peak positive value of the filtered pressure signal following each infusion pulse of the infusion device.

51. A method for detecting an open fluid line as defined in claim 50, wherein:

the step of comparing includes steps of
monitoring the filtered pressure signal and producing a peak positive signal indicative of the peak positive value thereof following each infusion pulse of the infusion device,
amplifying the peak positive signal by a prescribed negative fraction to produce the negative threshold signal, and
comparing the filtered pressure signal with a prescribed negative threshold signal; and the step of producing produces the alarm signal whenever the step of comparing determines that the filtered pressure signal is more negative than the threshold signal.

52. A method for detecting an open fluid line as defined in claim 51, wherein the negative fraction used in the step of amplifying is about negative two-thirds.

53. A method of detecting faults in the operation of a parenteral administration system wherein an infusion device infuses a parenteral fluid through a tube to the vascular system of a patient in a pulsing fashion, said method comprising:

monitoring the pressure of the fluid in the tube and producing a corresponding pressure signal;

evaluating the pressure signal over a period of time to detect characteristic patterns in the waveform of the pressure signal evaluated which are indicative of improper fluid communication between the fluid tube and the vascular system of the patient; and producing an alarm signal whenever such characteristic patterns are detected.

* * * * *

UNITED STATES PATENT AND TRADEMARK OFFICE
CERTIFICATE OF CORRECTION

PATENT NO. : 4,534,756

DATED : August 13, 1985

INVENTOR(S) : Peter E. Nelson

It is certified that error appears in the above-identified patent and that said Letters Patent is hereby corrected as shown below:

In Column 1, line 37-38, delete "satisfactorily" and insert therefor --satisfactory--.

In Column 2, line 65, after "with" delete "with".

In Column 4, line 60-61, delete "administrater" and insert therefor --administer--.

In Column 9, line 37, delete "witn" and insert therefor --with--.

In Column 10, line 31, delete "occuring" and insert therefor --occurring--.

In Column 11, line 50, delete "whenver" and insert therefor --whenever--.

In Column 11, line 54, delete "teh" and insert therefor --the--.

In Column 11, line 58, delete "6" and insert therefor --5--.

In Column 12, line 9, after "comparing" delete "if".

UNITED STATES PATENT AND TRADEMARK OFFICE
CERTIFICATE OF CORRECTION

PATENT NO. : 4,534,756
DATED : August 13, 1985
INVENTOR(S) : Peter E. Nelson

It is certified that error appears in the above-identified patent and that said Letters Patent is hereby corrected as shown below:

In Column 12, line 17, after "comparing" delete "if".

In Column 12, line 22, delete "8" and insert therefor --7--.

In Column 15, line 35, after "fluid" insert --tube--.

In Column 16, line 29, delete "alram" and insert therefor --alarm--.

In Column 18, line 56, delete "40" and insert therefor --46--.

Signed and Sealed this

Seventeenth Day of December 1985

[SEAL]

Attest:

DONALD J. QUIGG

Attesting Officer

Commissioner of Patents and Trademarks